United States Patent
Yang et al.

(10) Patent No.: US 6,306,638 B1
(45) Date of Patent: *Oct. 23, 2001

(54) MUTANT BIFIDOBACTERIA STRAINS WITH ACID, BILE SALT AND OXYGEN TOLERANCE

(75) Inventors: Yuann-Shiuann Yang; Mei-Ching Chen; Chii-Cherng Liao, all of Hsinchu (TW)

(73) Assignee: Food Industry Research and Development Institute, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 09/001,069

(22) Filed: Dec. 30, 1997

Related U.S. Application Data

(63) Continuation of application No. 08/735,263, filed on Oct. 22, 1996, now Pat. No. 5,711,977.

(51) Int. Cl.$^7$ ............... A23C 17/00; C12N 1/00; C12N 1/12; C12N 1/20; C12N 1/38
(52) U.S. Cl. ............... 435/252.1; 426/61; 426/71; 435/243; 435/244; 435/822
(58) Field of Search ............... 435/252.1, 243, 435/244, 822; 426/61, 71

(56) References Cited

U.S. PATENT DOCUMENTS

| | | | |
|---|---|---|---|
| 4,087,559 | 5/1978 | Mutai | 426/43 |
| 4,091,117 | 5/1978 | Mutai | 426/43 |
| 4,187,321 | 2/1980 | Mutai | 426/43 |
| 4,870,022 | 9/1989 | Sozzi | 435/252.1 |
| 5,087,449 | 2/1992 | Masai | 424/195.1 |
| 5,192,685 | 3/1993 | Yasui | 435/252.1 |
| 5,322,836 | 6/1994 | Tomita | 514/6 |
| 5,494,664 | 2/1996 | Brassart | 424/93.4 |
| 5,501,857 | 3/1996 | Zimmer . | |

FOREIGN PATENT DOCUMENTS

| | | |
|---|---|---|
| 47-29995 | 8/1972 | (JP) . |
| 57-99190 | 6/1982 | (JP) . |
| 59-53829 | 12/1984 | (JP) . |
| 61-185182 | 8/1986 | (JP) . |
| 61-205481 | 9/1986 | (JP) . |
| 4-320642 | 11/1992 | (JP) . |

OTHER PUBLICATIONS

Kim et al., Culture conditions and growth characteristics of Bifidobacterium longum; J. Microbiol. Biotechnol. , see abstract, 1995.*
Shimamura et al., 1992 J. Dairy Sci. 75:3296–3306.
Grill et al., 1995 Current Microbiol. 31:23–27.
Lankaputhal et al., 1995 Cultured Dairy Products Journal 30:2–7.
Clark and Martin, Selection of Bifidobacteria for Use as Dietary Adjuncts in Cultured Dairy Foods: III—Tolerance to Simulated Bile Concentrations of Human Small Intestines, Cult. Diary Prod. J. 29:18–21 (1994).
Holcomb et al. Viability of Lactobacillus Acidophilus and Bifidobacterium Bifidum in Soft–Serve Frozen Yogurt, Cultured Dairy Products Journal 26:4–5 (1991).
Klaver and van der Meer, The Assumed Assimilation of Cholesterol by Lactobacilli and Bifidobacterium bifidum Is Due to Their Bile Salt–Deconjugating Activity, Applied & Environmental Microbiology 59:1120–1124 (1993) Umada, Applications of bifidobacterium in milk fermentation, New Food Industry 24:63–70 (1982).
Fukudai, Characteristics of bifidobacterium used to produced fermented milk, New Food Industry 20:17–23 (1980).
Singh et al., "Microencapsulation of Bifidobacterium Longum for use in Food", Abstract 89B–6, Book of Abstracts, 1996 IFT Meeting, New Orleans, LA.
Yang et al., "Breeding of Bifidobacteria isolated in Taiwan with stress tolerance", Abstract 89B–7, Book of Abstracts, 1996 IFT Meeting, New Orleans, LA.
Pochart et al., Survival of Bifidobacteria Ingested Via Fermented Milk During Their Passage Through The Human Small Intestine: An In Vivo Study Using Intestinal Perfusion, Am. J. Clin. Nutr. 55:78–80 (1992).
Berrada et al., Bifidobacterium from Fermented Milks: Survival During Gastric Transit, J. Dairy Sci. 74:409–413 (1991).
Ibrahim and Bezkorovainy, Survival of Bifidobacteria in the Presence of Bile Salt, J. Sci. Food Agric. 62:351–354 (1993).

* cited by examiner

Primary Examiner—David M. Naff
Assistant Examiner—Deborah K. Ware
(74) Attorney, Agent, or Firm—Fish & Richardson P.C.

(57) ABSTRACT

Bifidobacteria strains and mutants thereof having tolerance in the gastrointestinal environments and to a method for culturing the same. Strains of the invention include *Bifidobacterium longum* ATCC No.(s) 55815, 55816, 55817 and 55818. All of which have tolerances against bile salt, acid and oxygen and which have been obtained through mutagenesis and screening for tolerances against bile salt, acid and oxygen by using acid tolerant using acid-tolerant *Bifidobacterium longum* Y1 and Y2 strains (ATCC 55813 and 55814). These strains can be isolated from healthy infant feces as the parent strains. Further, an isolated Bifidobacterium mutant strain which grows aerobically, is ten times more tolerant to hydrochloric acid at a pH of 1.5 to 4.5 and is also tolerant to oxgall at 0.3% in a culture medium is disclosed. The strains show excellent growth under aerobic condition in the presence of skim milk without supplement of other growth promoting substances. The oxygen-tolerant property of the strains makes them useful for industrial production. In addition, food products containing the strains are also disclosed.

20 Claims, No Drawings

MUTANT BIFIDOBACTERIA STRAINS WITH ACID, BILE SALT AND OXYGEN TOLERANCE

This application is a continuation application of U.S. patent application Ser. No. 08/735,263 filed Oct. 22, 1996, now U.S. Pat. No. 5,711,977.

FIELD OF THE INVENTION

The present invention relates to Bifidobacterium strains and to a method for culturing these strains.

BACKGROUND OF THE INVENTION

The presence of Bifidobacterium in an infant's intestine is typically an indication of a healthy intestinal bacterial flora. While types and sizes of Bifidobacterium populations vary with age, bifidobacteria are present throughout the life cycle of a human being.

Bifidobacteria have various physiological properties. For instance, these bacteria can inhibit putrefactive and pathogenic bacteria, maintain a normal intestinal bacterial population, inhibit production of toxic amines, synthesize vitamin B groups, and produce L-lactic acid.

Since bifidobacteria tend to be more anaerobic than other lactic acid-producing bacteria, the development of food products containing viable bifidobacteria has encountered problems such as difficulties in maintaining bacterial viability during storage of the food products. In addition, orally administered bacteria are under the stress caused by, e.g., gastric acid and bile salt encountered in the gastrointestinal environment.

Nearly a hundred different kinds of bifidobacteria-containing food products have been developed to date, yet none of the strains used in these products are tolerant to oxygen, gastric acid, and bile salt. Many strains disclosed in the prior art, for example, are acid- and oxygen-tolerant, yet few of them are bile salt-tolerant (see, e.g., Tables I and II).

According to some studies, Bifidobacterium spp. ATCC 15700, ATCC 15696, ATCC 15697, and ATCC 15707 have extremely low growing abilities when cultured in the presence of 0.3% glycocholate for 24 hours. Studies of acid-tolerant strains have been devoted largely to the bacterial viability in acidic dairy products (pH 4 to 4.8) over a period of storage under refrigerating conditions. Some studies carried out to test tolerance to gastric acid set pH values at about 3 to 3.5 and not at about 2, which occurs during secretion of gastric acid.

SUMMARY OF THE INVENTION

Accordingly, an object of the present invention is to provide a gastric acid-tolerant strain of *Bifidobacterium longum* isolated from healthy infants' feces, and based on the isolated strain, to provide strains having multiple characteristics such as tolerance to gastric acid, bile salt and oxygen by means of artificial mutagenesis and screening.

Within the scope of the invention are isolated Bifidobacterium strains characterized by their ability to grow aerobically (e.g., in the open air) and their tolerance to hydrochloric acid at a pH of approximately 1.5 to 4.5 (e.g., 2.0), and its tolerance to oxgall at approximately 0.3% (weight/volume or "w/v") in a culture medium. By "tolerance to hydrochloric acid at a pH of approximately 1.5 to 4.5" is meant that the strain has a survival rate of $10^{-6}$ or higher (e.g., $10^{-5}$ or $10^{-4}$) in a physiological saline buffer containing hydrochloric acid at about pH 1.5–4.5 (see, e.g., Tables III and IV, infra, and the accompanying text). By "tolerance to oxgall at approximately 0.3%" is meant that bacteria from the strain can grow (i.e., proliferate) in the presence of oxgall present at about 0.3%

TABLE I

Comparison of patented bifidobacteria strains with the invention strains

| Strains | Inventors | Isolation sources | Characteristics | Assignee | Reference |
|---|---|---|---|---|---|
| *Bifidobacterium bifidum* YIT-4002 (FERM-P 3371) | Mutai et al. | Feces of healthy infants fed with mother milk | 1. Aerobic growth without growth promoting substance *Growth up to $5.0 \times 10^9$ CFU/ml in the presence of 6.5 ppm oxygen over 24 hrs. and up to $6.5 \times 10^9$ CFU/ml in the presence of 0.1 ppm oxygen over 24 hrs.. | Yakult Honsha | U.S. Pat. No. 4087559 (1978) |
| *B. bifidum* YIT-4005 (FERM-P 3372) | Mutai et al. | same as above | 1. Oxygen tolerance: results of growth are the same as that of anaerobic growth and can be up to $10^9$ CFU/ml. 2. Acid tolerance: 4% survived after storing at pH 4.2 for 7 days (similar results obtained both in milk and buffer solution). | Yakult Honsha | U.S. Pat. No. 4091117 (1978) JP second publication No. Sho-56-42250 (1981) |
| *B. breve* YIT-4006 (FERM-P 3906) | Mutai et al. | Same as above | 1. Growth with tolerance against oxygen in absence of growth promoting substances and can be up to $10^9$ CFU/ml | Yakult Honsha | U.S. Pat. No. 4187321 (1980) JP second publication No. Sho-59-53031 |

TABLE I-continued

Comparison of patented bifidobacteria strains with the invention strains

| Strains | Inventors | Isolation sources | Characteristics | Assignee | Reference |
|---|---|---|---|---|---|
| B. breve HW-107 (FERM 5774) | Ishikawa et al. | Feces of healthy infant fed with milk | after 24 hrs. 1. Acid tolerance (gastric acid): pH 3.5, 37° C./1 hr., bacteria population decreased 3.89 log value (buffer system). | Midorina Co., Ltd. | (1984) JP first publication No. Sho-57-99190 (1982) |
| B. longum M-8201 (FERM 6548) | Kawashima et al. | Feces of healthy infant fed with milk | 1. Acid tolerance: 11.8% survived after storing at pH 4.6 for 7 days (buffer system); 53.6% survive after storing at pH 4.8 for 7 days (milk system). | Morinaga Milk Industry Co., Ltd. | JP second publication No. Sho-59-53829 (1984) |
| B. breve SBR 3212 (FERM 11915) | Yoshino et al. | Feces of healthy infant born several months and fed with mother milk | 1. Acid tolerance: 8% survived after storing at pH 4.0 for 7 days (milk system) and 23% (buffer system). 2. Oxygen tolerance: growth increased 10-fold after 24 hour culturing and kept at 5-fold increase after 48 hrs.. | Snow brand Milk Prod Co., Ltd. | JP first publication No. Hei-4-320642 (1992) |
| B. infantis CNCM T-372 B. bifidum CNCM I-373 B. breve CNCM I-374 | Sozzi | | 1. Acid tolerance: survivabilities after storing at pH 4.0 for 7 days were 100% (I-372), 75% (I-373), and 70% (I-374); and after 40 days, 70% (I-372), 60% (I-373) and 14% (I-374) (milk system). 2. Oxygen tolerancing substances with growth promoting substances | Nestec S.A. (Switzerland) | U.S. Pat. No. 4870020 (1989) JP first publication No. Sho-61-205481 (1986) EP 86101202 (1986) |
| B. longum No. 1022 (FERM-P 8033) | Mura et al. | UV mutant of B. longum ATCC 15708 | 1. Acid tolerance: after storing at pH 4.7 for 7 days, survivability of original B. longum ATCC 15708 is only 7% of that of mutant | Mei Ji Milk Industry Co., Ltd. | JP first publication No. Sho-61-185182 (1986) |
| B. breve M 7204 (FERM1324) | Kawashima et al. | | 1. Acid tolerance: 0.02% survived after storing at pH 4.6 for 7 days (buffer system); 1.5% survived after storing at pH 4.8 for 7 days (milk system) | Morinaga Milk Industry Co., Ltd. | JP second publication No. Sho-47-29995 (1972) |
| B. longum ATCC 55816 | | Feces of healthy infant | 1. Gastric acid tolerance: population decreased 3–4 log value after treatment at pH 2, 37° C./2 hr (0.85% NaCl/0.01 N HCl system) 2. Tolerance to bile salt: growth up to $10^8$–$10^9$ CFU/ml in the presence of 0.3% oxgall for 24 hrs. 3. Oxygen tolerance: growth up to $10^9$ | | The present invention |

TABLE I-continued

Comparison of patented bifidobacteria strains with the invention strains

| Strains | Inventors | Isolation sources | Characteristics | Assignee | Reference |
|---|---|---|---|---|---|
| | | | CFU/ml for 24 hrs. without growth promoting substances. | | |

TABLE II

Comparison of Tolerant Strains Disclosed in the Literature with the Invention Strains

| Strains | Isolation sources | Characteristics | Research Unit | References |
|---|---|---|---|---|
| *B. longum* TQB 21-2-2 | Feces of mid-age men | 1. Oxygen tolerance: growth increased 25% after thin layer standing for 24 hrs.; and increased 25% after shaking for 60 hrs.. | Ten-jin Light Industries College | Been Fa, Sheu et al. (1994) |
| *B. bifidum* | | 1. Oxygen tolerance: growth up to $10^9$ CFU/ml after non-anaerobic culturing for 5–7 hrs. (milk system). 2. Acid tolerance; 13.5% survived after storing at pH 4.5 for 10 days (milk system). | Wuu-Hann Light Industries Research Institute | Sheau Chau, Fuh et al. (1990, 1992) |
| *B. bifidum* GSNE | Feces of infant fed with milk | 1. Oxygen tolerance: Growth increased 1.3 log value in the presence of 6.2–6.4 ppm dissolved oxygen for 24 hrs., and 1.8 log value in the presence of 0 ppm dissolved oxyyen for 24 hrs. (milk system). | Yakult Honsha Research Institute | Wumada (1982) |
| *B. bifidum* *B. breve* | | 1. Gastric acid tolerance: Population decreased 5.3 and 2.6 log values, respectively, after culturing at pH 3, 37° C. for 3 hrs. (0.2% NaCl, 0.32% pepsin system). 2. Bile salt tolerance: growth rate in the presence of 135 ppm bile salt were 67% and 45%, respectively (culture medium system). | Same as above | Mutai (1978) |
| *B. longum* | | 1. Bile salt tolerance: population decreased 2.01 log value at 2% oxgall, 37° C. for 12 hr (distilled water system). | Mississippi State University | Clark and Martin (1994) |
| *Bifidobacterium* Bb-12 | | 1. Acid tolerance: 100% survived at pH 3 for 2 hrs. (MRS liquid culturing medium system). 2. Bile salt tolerance: 100% survived at 0.5% oxgall, 37° C. for 2 hrs. (milk plus yeast extract system). | Chr. Hansen's Lab. | Hoier (1992) |
| *B. longum* ATCC 55816 | Feces of healthy infant | 1. Gastric acid tolerance: population decreased 3–4 log value after treatment at pH 2, 37° C./2 hr (0.85% NaCl/0.01N HCl system). 2. Bile salt tolerance: growth up to $10^8$–$10^9$ CFU/ml in the presence of 0.3% oxgall for 24 hrs.. 3. Oxygen tolerance: growth up to $10^9$ CFU/ml for 24 hrs. without growth promoting substance. | | The present invention |

(w/v) in a culture medium (see, e.g., Table IV, infra, and the accompanying text).

Exemplary strains of the invention can have the same (i.e., the difference is less than 10%) viability rate in a medium containing approximately 0.3% oxgall as in a medium containing no oxgall (see, e.g., Table IV, infra). The strains of the invention include, but are not limited to, *Bifidobacterium longum* Y1 (ATCC 55813) and Y2 (ATCC 55814). Indeed, also within the scope of this invention are (i) mutants of Y1, e.g., *B. longum* Y1-2E-05 (ATCC 55815) and *B. longum* Y1-4A-01 (ATCC 55816), (ii) mutants of Y2, e.g., *B. longum* Y2-1A-01 (ATCC 55817) and *B. longum*

Y2-2B-04 (ATCC 55818), and (iii) mutants of *B. longum* Y1-2E-05, *B. longum* Y1-4A-01, *B. longum* Y2-1A-01, and *B. longum* Y2-2B-04.

The invention also features food products containing a food stuff (e.g., yogurt, sour milk, lactic fermentation beverage, soymilk, candy, ice cream, milk, milk powder and the like) and bacteria of one or more of the strains of this invention.

Unless otherwise defined, all technical and scientific terms used herein have the same meaning as commonly understood by one of ordinary skill in the art to which this invention belongs. Exemplary methods and materials are described below. However, methods and materials similar or equivalent to those described herein can be also used to obtain the strains of the present invention. All publications mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

DETAILED DESCRIPTION OF THE INVENTION

Deposition of Mutant Microorganisms
(1) The description of microorganism mutants The subject microorganisms of the present invention include acid-tolerant strains of *Bifidobacterium longum* Y1 and Y2 as parent strains (American Type Culture Collection ("ATCC") 55813, and ATCC 55814), both of which were isolated from feces of healthy infants; and mutant strains *B. longum* Y1-2E-05 (ATCC 55815), *B. longum* Y1-4A-01 (ATCC 55816), *B. longum* Y2-1A-01 (ATCC 55817), and *B. longum* Y2-2B-04 (ATCC 55818). The former two mutant strains were obtained by mutagenetic modification using *B. longum* Y1 as the parent strain, and the latter two were similarly obtained using *B. longum* Y2 as the parent strain.

The strains of the present invention are characterized by possessing simultaneous tolerance to bile salt and gastric acid (which exist in the gastrointestinal environment), as well as to oxygen, which is commonly used in industrial culturing.

Exemplary strains of the present invention which are described throughout this disclosure, have been deposited at ATCC under the Budapest Treaty the American Type Culture Collection, 10801 University Blvd., Manassas, Va. 20110–2209. The dates and accession numbers of the deposits are as follows:

| Name of microorganism | Deposition date | Number |
| --- | --- | --- |
| B. longum Y1 | August 29, 1996 | ATCC 55813 |
| B. longum Y2 | August 29, 1996 | ATCC 55814 |
| B. longum Y1-2E-05 | August 29, 1996 | ATCC 55815 |
| B. longum Y1-4A-01 | August 29, 1996 | ATCC 55816 |
| B. longum Y2-1A-01 | August 29, 1996 | ATCC 55817 |
| B. longum Y2-2B-04 | August 29, 1996 | ATCC 55818 |

(2) Generation of strains having multiple tolerance

The bacterial strains of the present invention can be generated by, for example, mutagenesis of a parent strain having one to two, but not all three, of the desired tolerances. Mutagenesis of a parent strain with triple tolerances may also result in mutated strains with improved tolerance. Alternatively, the bacterial strains of the present invention can be isolated from the gastrointestinal environment or feces of a human.

Strategies and methods of mutagenesis, procedures for screening and isolation of mutated bacterial strains, compositions of media used in producing the mutant strains of the invention will be described in detail in the Examples below.
(3) Verification of Tolerance After a mutant strain is generated, it is tested as follows for its ability to grow aerobically (i.e., tolerance to oxygen) and its tolerance to bile salt and gastric acid.

(i) Bile salt tolerance

Oxgall has been commonly used in culture media for selective culturing of human intestinal bacteria, and its effect on bacterial growth is believed to be very similar to that of human bile salt. The average oxgall concentration used is 0.3% (w/v).

After being properly activated, 1% of each of the mutant strains and their corresponding parent strains can be inoculated into the basic medium MRS supplemented with (test group) or without (control group) 0.3% oxgall. After culturing for about 24 hours, the optical densities ("OD") at 600 nm of the cultures and the percentages of survived bacteria are then measured and compared to verify the bacteria's tolerance to bile salt.

(ii) Acid tolerance

The pH value of gastric acid varies in the range of about 1.5–4.5 in a period of 2 hours, depending on the entering time and the type of gastric contents. In the present invention, pH 2 can be used as a representative gastric pH value. Since gastric acid is similar in nature to hydrochloric acid, physiological saline with pH adjusted to 2 by HCl can be used to treat the bacteria at 37° C. for 2 hours. The percentage of the survived bacteria are then measured and compared with that of the group treated with physiological saline at pH 7 to verify the bacteria' tolerance to acid.

(iii) Oxygen tolerance

To test the new strains' tolerance to oxygen, the new strains were inoculated into a conventional spiral test tube after being properly activated, and cultured by standing under a non-anaerobic condition for 24 hours. Subsequently, the OD 600 nm and the bacterial population of the cultures were measured and compared with those of the bacteria cultured under an anaerobic condition.

(4) Assessment of bacteria survival

To assess bacterial survival after various treatments, 1 ml of a test sample containing cultured bacteria can be mixed with 9 ml of a dilution solution containing 0.1% peptone and 0.1% agar. A series of appropriate dilutions is then prepared, and 1 ml of each dilution is mixed with about 20 ml of MRS solid medium (molten state, about 45° C.) and added to a petri dish. The petri dish is swirled gently and let stand at room temperature. After the medium is completely solidified, the plate is flipped upside down and incubated in an anaerobic jar at 37° C. for 2 to 3 days. The number of bacterial colonies on the plate is then recorded.

(5) Culturing of the new strains

The strains of the present invention can be cultured aerobically in skim milk without addition of growth promoting substance.

(6) Applications of the new strains

The strains of the present invention can be used alone or in combination with two or more different strains of lactic acid-producing bacteria (e.g., *Lactobacillus acidophilus, Lactococcus lactis, Lactobacillus casei, Streptococcus thermophilus, Lactobacillus bulgaricus*), yeast (e.g., *Candida kefyr, Saccharomyces florentinus*), or any other usable strains as inoculum in fermentation processes to yield food products such as yogurt, sour milk, frozen yogurt, lactic fermentation beverage, or fermented soy milk. The strains of the present invention can also be food additives for use during preparation of foodstock, or to be added at a later stage of a fermentation process without involved in the fermentation. As such, they can be used in a variety of products, such as milk, concentrated milk, milk powder, ice cream, soy milk, deserts, candy, baby food, products of lactic fermentation milk, and fermentation products described above. The amount of the bacteria added to each product can yield a bacterial count of $10^6$ to $10^9$ cfu (i.e., colony forming unit) per gram or milliliter.

In another type of application, the strains of the present invention or the above-described products can be used to prepare frozen or lyophilized powders which contain about $10^9$ or more viable bifidobacteria per gram of food product. These powders can be used alone or in combination with yeast powder, carbohydrates or other fillers to generate tablets or capsules useful in, e.g., assisting digestion or conditioning intestines.

Effectiveness of the Present Invention

The strains of the present invention can pass through stomach with increased survivability, as compared to many previously known Bifidobacterium strains. The strains of the present invention, which include mutant strains of Bifidobacterium, have tolerances to bile salt, gastric acid and oxygen. The oxygen tolerance of the new strains greatly simplifies the procedure for their culturing or storage, since the culturing and storage can be carried out with neither anaerobic equipment nor continuous nitrogen purging. In addition, with combined resistances to gastric acid and bile salt, the new strains can survive the harsh environments of the gastrointestinal tract and remain effective after oral administration.

The following examples are meant to illustrate the strains, methods, and compositions of the present invention. Suitable modifications and adaptations of the described conditions and parameters that are obvious to those skilled in the art are within the spirit and scope of the present invention.

EXAMPLE 1

Culturing and Storing of Inoculum

*Bifidobacterium longum* ATCC 55813 and ATCC 55814 as well as mutant strains thereof were cultured in MRS (de Man Rogasa and Sharpe) medium. When culturing was performed in liquid state, test tubes having rubber stoppers of anaerobic type were used as vessels (Bellco Glass, Inc.) and an anaerobic operation system (Virginia Polytechnic Institute ("V.P.I.")) was used to inoculate the bacterial strains in an atmosphere of gas mixture containing 90% nitrogen and 10% carbon dioxide. When culturing was formed in solid state, the strains were inoculated into a plate containing solid medium and then the plate was placed upside down in an anaerobic jar. For storage, the strains were inoculated into MRS liquid medium containing 10% glycerol and then frozen stored at $-80°$ C.; or were added to 20% skim milk, lyophilized, and stored at $4°$ C. until use.

The composition of MRS medium is as follows:

| | |
|---|---|
| Proteose peptone No. 3 | 10.0 g |
| Beet extract | 10.0 g |
| Yeast extract | 5.0 g |
| Dextrose | 20.0 g |
| Tween 80 | 1.0 g |
| Ammonium citrate | 2.0 g |
| Sodium acetate | 5.0 g |
| $MgSO_4 \cdot 7H_2O$ | 0.1 g |
| $MnSO_4 \cdot H_2O$ | 0.05 g |
| $K_2HPO_4$ | 2.0 g |
| Distilled water | 1.0 L | pH 6.2 to 6.5

EXAMPLE 2

Isolation and Screening of Bacterial Strains

Feces from healthy infants were inoculated into two kinds of selective media: BL-LPIM (BL agar supplemented with 2 g/l lithium chloride, 2 mg/l metronidazole, 0.025 g/l sodium iodoacetate, and 3 g/l sodium propionate), and BIM (Reinforced Clostridial Agar supplemented with 0.02 g/l nalidixic acid, 0.0085 g/l polymyxin B sulfate, 0.05 g/l kanamycin sulfate, 0.025 g/l sodium iodoacetate, 0.025 g/l 2,3,5-tri-phenyltetrazolium chloride). Totally 194 strains of Bifidobacterium spp. were isolated. Tolerances of these strains to acid, bile salt and oxygen were assessed. Two strains that are potentially tolerant of acid, i.e., ATCC 55813, and ATCC 55814, were obtained, both of which were identified by the method recommended in Bergey's Manual as *Bifidobacterium longum*. The bacteriological characteristics of the two strains are as follows.

1. Morphological characteristics

ATCC 55813 and ATCC 55814 were classified as gram-positive bacteria. Under microscopic examination, they had a rod-like bar, Y-shaped, twisted, arc, or V-shaped form, with occasional expanded form or node. Circular protruded, bright, smooth, white colonies with sizes of about 1–4 mm were formed on the surface of MRS solid medium, while colonies inside the medium appeared as circular flying saucer or star-like triangle. Colonies at the bottom of the medium formed white, saw-toothed edged, corona-shaped metabolic products, with sizes varying from about 3 to 8 mm.

2. Culturing Characteristics

The bacteria could grow at 25–42° C., with the optimal temperature being 37–42° C. The pH in the culture medium could range from 5 to 9, with the optimal pH being pH 6.5–7.5. After anaerobic culturing in MRS liquid medium, the ratio of acetic acid to lactic acid formed in the medium by the bacteria was about 1.5.

3. Physiological properties

The following are some physiological properties of ATCC 55813 and ATCC 55814. "+" in the parenthesis denotes positive, while "−" denotes negative.

Catalase activity (−)
gas generation test (−)
milk coagulation activity (+)
gelatin hydrolyticity (−)
nitrate reducing activity (−)
indole formation test (−)
hydrogen sulfide generation test (−)

4. Utilization of carbon source

Carbon sources that yielded positive responses in fermentation were xylose, melibiose, galactose, glucose, arabinose, lactose, fructose, raffinose, maltose, ribose, sucrose, mannose, and melizitose. Those that yielded negative responses in fermentation were mannitol, sorbitol, cellobiose, trehalose, inulin, glycogen, starch, salicin, amygdalin, rhamnose, meso-erythritol, glycerol, meso-inositol, and glucuronic acid.

EXAMPLE 3

Improvement of Inoculum

1. UV mutagenesis

After being activated twice in MRS medium at 37° C., suspensions of ATCC 55813 and ATCC 55814 were inoculated at 2% (v/v) to 10 ml of broth solution and cultured for 18–24 hours. The bacteria were then harvested, washed 3 times with 0.1 M magnesium sulfate solution, and re-suspended in the same solution. The bacteria suspension was placed in a sterile glass dish and irradiated under UV STRATALINKER™ 1800 (Stratagene) at 250 erg UV dosage. Irradiated bacteria were transferred to MRS medium and cultured overnight. 0.2 ml of the bacteria suspension were applied to the solid screening medium, and cultured at 37° C. for 3–4 days.

2. NTG mutagenesis

ATCC 55813 and ATCC 55814 were cultured in MRS medium and harvested in the same manner as described above. The bacteria were then washed with 0.1 M phosphate buffer solution (pH 7.0; "PBS"), treated with 200 µg/ml of a mutation agent, N-methyl-N'-nitro-N-nitrosoguanidine ("NTG") at 37° C. for 30 minutes, centrifuged, and washed twice with PBS to remove residual NTG. After washing, the bacteria were re-suspended in MRS medium and cultured overnight. 0.2 ml of the bacteria suspension was then applied to the solid screening medium and cultured at 37° C. for 3–4 days.

3. Screening media

The medium for acid tolerance screening was MRS solid medium with its pH adjusted to about 4–5 with 4 M HCl.

The medium for bile salt tolerance screening was MRS solid medium supplemented with 0.3% (w/v) oxgall juice.

Tolerance potential of the selected strains was verified by the above-described tests. Verified strains were subjected to further mutant screening to produce strains with multiple tolerances. As shown in Table III, the mutant strains could grow up to $10^8$–$10^9$ cfu/ml in the presence of bile salt over 24 hours. Such growth rate was nearly $10^6$–$10^8$ fold higher than that of the parent strain. Furthermore, the acid tolerance of the mutant strains remained at a level similar to that of their corresponding parent strain: After acid treatment, the population of both the mutant strains and their parents decreased by approximately 10,000 folds (Table III). In addition, the mutant strains could grow well under non-anaerobic conditions (Table III).

EXAMPLE 4

Large Scale Culturing

The mutant strains, e.g., ATCC 55815, ATCC 55816, ATCC 55817, and ATCC 55818, were cultured in 10 ml of MRS liquid medium by standing at 37° C. for 18–24 hours. The bacteria suspensions were then inoculated at an amount of 1% to 300 ml MRS liquid medium in a 500 ml Erlenmeyer flask and cultured under the same conditions for 18–24 hours. The resultant bacteria were tested for their tolerance properties. The results showed that the mutant bacteria cultured at a large scale displayed a tolerance level similar or even superior to the corresponding bacteria cultured at a smaller scale.

EXAMPLE 5

Characteristics of the New Strains

As described in Table IV, the mutant strains described above showed higher level of bile salt and acid-tolerances that the standard strains of the same genus, i.e., *B. longum* ATCC 15707, *B. bifidum* ATCC 29521, *B. breve* ATCC 15700, and *B. breve* ATCC 15701. The acid tolerance of the mutant strains is about 10 times more tolerant to HCl than Bifidobacterium strain ATCC 15707 as shown by Table IV.

TABLE III

Tolerance Level of Isolated Strains and Mutant Strains

| Strains | Bile salt tolerance $OD_{600nm}$ | | Acid Tolerance Count decreased in log value[c] | Oxygen Tolerance $OD_{600nm}$ | |
|---|---|---|---|---|---|
| | Control[a] | Test[b] | | Anaerobic | Non-anaerobic[d] |
| B. longum ATCC 55813 | 2.3668 | 0.1000 | −3.93 | 2.3668 | 2.3560 |
| B. longum ATCC 55814 | 2.6511 | 0.1600 | −3.56 | 2.6511 | 1.5020 |
| B. longum ATCC 55815 | 2.3634 | 1.5800 | −3.96 | 2.3634 | 2.0490 |
| B. longum ATCC 55816 | 2.0054 | 1.4807 | −3.66 | 2.0054 | 1.4834 |
| B. longum ATCC 55817 | 2.6920 | 1.6740 | −3.68 | 2.6920 | 2.2320 |
| B. longum ATCC 55818 | 2.3832 | 1.2652 | −4.27 | 2.3832 | 1.4629 |

[a]Bacteria were cultured in MRS broth for 24 hours.
[b]Bacteria were cultured in MRS broth plus 0.3% oxgall for 24 hours.
[c]The values were obtained by subtracting the bacterial count in log value after treatment with pH 7.0 physiological saline for 2 hours from the corresponding count after treatment with pH 2.0 saline for 2 hours.
[d]Bacteria were cultured in a non-anaerobic spiral tube (MRS broth) for 24 hours (the initial $OD_{600nm}$ was about 0.2).

TABLE IV

Comparison of tolerance levels among new strains of the present invention and standard strains

| Strains | Bile salt tolerance Count in log value | | Acid Tolerance Count decreased in log value[c] |
|---|---|---|---|
| | Control[a] | Test[b] | |
| B. bifidum ATCC 29521 | 8.62 | <3.00 | −5.50 |
| B. longum ATCC 15707 | 9.22 | <3.00 | −5.59 |
| B. breve ATCC 15700 | 8.88 | 4.04 | −7.33 |

TABLE IV-continued

Comparison of tolerance levels among new strains of the present invention and standard strains

| Strains | Bile salt tolerance Count in log value | | Acid Tolerance Count decreased in log value[c] |
|---|---|---|---|
| | Control[a] | Test[b] | |
| B. breve ATCC 15701 | 8.91 | 4.94 | −8.30 |
| B. longum ATCC 55815 | 9.53 | 8.91 | −4.32 |
| B. longum ATCC 55816 | 9.26 | 8.85 | −4.06 |
| B. longum ATCC 55817 | 9.36 | 8.73 | −3.87 |
| B. longum ATCC 55818 | 9.16 | 8.98 | −4.43 |

[a]Viable counts of bacteria cultured in MRS broth for 24 hours.
[b]Viable counts of bacteria cultured in MRS broth plus 0.3% oxgall for 24 hours (higher log value indicates higher tolerance to bile salt.
[c](counts in log value after treatment with pH 2.0 physiological saline for 2 hours) − (count in log value after treating with pH 7.0 physiological saline for 2 hours) (less negative value indicates higher acid tolerance).

EXAMPLE 6

Culturing of the Strains

A 250 ml Erlenmeyer flask containing 125 ml of 12% reduced skim milk was sterilized at 115° C. for 20 minutes, and then inoculated with 2.5 ml of each of the mutant strains or a standard strain. The flask was let stand at 37° C. under an aerobic condition, with culture samples taken periodically for measurement of bacterial counts and pH values. The results indicated that the mutant strain B. longum ATCC 55816 could grow up to $1.14 \times 10^9$ cfu/ml under an aerobic condition for 22 hours without addition of growth promoting substances, and that this strain could maintain their growing ability and survivability up to 68 hours with a count of $3.49 \times 10^8$ cfu/ml.

Other Embodiments

It is to be understood that while the invention has been described in conjunction with the detailed description thereof, that the foregoing description is intended to illustrate and not limit the scope of the invention, which is defined by the scope of the appended claims.

Other aspects, advantages, and modifications are within the scope of the following claims.

What is claimed is:

1. An isolated Bifidobacterium mutant strain which grows aerobically, is about 10 times more tolerant to hydrochloric acid than Bifidobacterium at a pH of approximately 1.5 to 4.5, and is tolerant to oxgall at approximately 0.3% (w/v) in a culture medium.

2. The strain of claim 1, wherein the strain is tolerant to hydrochloric acid at a pH of approximately 2.0.

3. The strain of claim 1, wherein the strain has the same viability rate in a culture medium containing approximately 0.3% oxgall as in a culture medium containing no oxgall.

4. The strain of claim 2, wherein the strain has the same viability rate in a culture medium containing approximately 0.3% of oxgall as in a culture medium containing no oxgall.

5. The strain of claim 1, wherein the strain is a mutant having all of the indentifying characteristics of *Bifidobacterium longum* Y1 (ATCC 55813).

6. The strain of claim 1, wherein the strain is a mutant having all of the indentifying characteristics of *Bifidobacterium longum* Y2 (ATCC 55814).

7. The strain of claim 1, wherein the strain is a mutant having all of the indentifying characteristics of *Bifidobacterium longum* Y1-2E-05 (ATCC 55815).

8. The strain of claim 1, wherein the strain is a mutant having all of the indentifying characteristics of *Bifidobacterium longum* Y1-4A-01 (ATCC 55816).

9. The strain of claim 1, wherein the strain is a mutant having all of the indentifying characteristics of *Bifidobacterium longum* Y2-1A-01 (ATCC 55817).

10. The strain of claim 1, wherein the strain is a mutant having all of the indentifying characteristics of *Bifidobacterium longum* Y2–2B-04 (ATCC 55818).

11. A food product comprising a food stuff and the strain of claim 1.

12. A food product comprising a food stuff and the strain of claim 2.

13. A food product comprising a food stuff and the strain of claim 3.

14. A food product comprising a food stuff and the strain of claim 4.

15. A food product comprising a food stuff and the strain of claim 5.

16. A food product comprising a food stuff and the strain of claim 6.

17. A food product comprising a food stuff and the strain of claim 7.

18. A food product comprising a food stuff and the strain of claim 8.

19. A food product comprising a food stuff and the strain of claim 9.

20. A food product comprising a food stuff and the strain of claim 10.

\* \* \* \* \*